United States Patent
Dolan (10) Patent No.: US 9,999,505 B2
(45) Date of Patent: Jun. 19, 2018

(54) METHOD FOR STABILIZING A CARDIAC VALVE ANNULUS

(71) Applicant: Medtronic Vascular, Inc., Santa Rosa, CA (US)

(72) Inventor: Mark Dolan, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 41 days.

(21) Appl. No.: 15/212,323

(22) Filed: Jul. 18, 2016

(65) Prior Publication Data
US 2016/0324638 A1 Nov. 10, 2016

Related U.S. Application Data

(63) Continuation of application No. 14/047,345, filed on Oct. 7, 2013, now Pat. No. 9,421,099, which is a continuation of application No. 11/739,526, filed on Apr. 24, 2007, now Pat. No. 8,551,161.

(60) Provisional application No. 60/745,557, filed on Apr. 25, 2006.

(51) Int. Cl.
*A61F 2/04* (2013.01)
*A61F 2/24* (2006.01)

(52) U.S. Cl.
CPC .......... *A61F 2/2445* (2013.01); *A61F 2/2466* (2013.01); *A61F 2/2442* (2013.01); *A61F 2210/0014* (2013.01); *A61F 2220/0016* (2013.01); *A61F 2230/0004* (2013.01); *A61F 2230/0008* (2013.01)

(58) Field of Classification Search
CPC ............................ A61F 2/2442–2/2448; A61F 2220/00–2220/0016
See application file for complete search history.

(56) References Cited

U.S. PATENT DOCUMENTS

| | | |
|---|---|---|
| 5,728,068 A | 3/1998 | Weissinger et al. |
| 6,702,844 B1 | 3/2004 | Lazarus |
| 6,932,838 B2 | 8/2005 | Schwartz et al. |
| 7,128,754 B2 | 10/2006 | Bolduc |
| 2002/0002401 A1 | 1/2002 | McGuckin et al. |
| 2002/0010504 A1 | 1/2002 | Alt |
| 2002/0099439 A1 | 7/2002 | Schwartz et al. |
| 2003/0018377 A1 | 1/2003 | Berg et al. |
| 2003/0199975 A1 | 10/2003 | Gabbay |
| 2003/0199987 A1 | 10/2003 | Berg et al. |
| 2004/0243230 A1 | 12/2004 | Navia et al. |
| 2004/0260393 A1 | 12/2004 | Randert et al. |
| 2004/0260394 A1 | 12/2004 | Douk et al. |
| 2005/0075584 A1 | 4/2005 | Call |

(Continued)

FOREIGN PATENT DOCUMENTS

| WO | WO02/094132 | 11/2002 | |
|---|---|---|---|
| WO | WO 2004112652 A2 * | 12/2004 | ......... A61B 17/0644 |

*Primary Examiner* — Yashita Sharma
*Assistant Examiner* — Rebecca Preston
(74) *Attorney, Agent, or Firm* — Medler Ferro Woodhouse & Mills (57) ABSTRACT

A method for stabilizing a cardiac valve annulus is provided. The method includes intravascularly delivering a prosthesis to a region of a cardiac valve, expanding the prosthesis to secure the prosthesis to the region of the cardiac valve, and reducing the inner diameter of the prosthesis to form the region of the cardiac valve into a predefined shape.

15 Claims, 7 Drawing Sheets

(56) References Cited

U.S. PATENT DOCUMENTS

| | | |
|---|---|---|
| 2006/0206203 A1 | 9/2006 | Yang et al. |
| 2006/0235509 A1 | 10/2006 | Lafontaine |
| 2006/0259136 A1 | 11/2006 | Nguyen |
| 2007/0027533 A1* | 2/2007 | Douk .................. A61F 2/2445 623/2.11 |
| 2008/0071364 A1 | 3/2008 | Kaye et al. |

* cited by examiner

METHOD FOR STABILIZING A CARDIAC VALVE ANNULUS

CROSS-REFERENCE TO RELATED APPLICATION

The present application is a Continuation of and claims priority to U.S. patent application Ser. No. 14/047,345, filed Oct. 7, 2013, now allowed, which is a Continuation of U.S. patent application Ser. No. 11/739,526, filed Apr. 24, 2007, now U.S. Pat. No. 8,551,161, which claims priority to U.S. Provisional Application 60/745,557, filed Apr. 25, 2006 the entire contents of which are incorporated herein by reference.

TECHNICAL FIELD

This invention relates generally to medical devices for treating cardiac valve regurgitation, particularly to a cardiac valve annulus reshaping system and method of using the same.

BACKGROUND OF THE INVENTION

Heart valves, such as the mitral, tricuspid, aortic and pulmonic valves, are sometimes damaged by disease or by aging, resulting in problems with the proper functioning of the valve. Heart valve problems generally take one of two forms: stenosis, in which a valve does not open completely or the opening is too small, resulting in restricted blood flow; or insufficiency, in which blood leaks backward across a valve when it should be closed. Valve replacement may be required in severe cases to restore cardiac function. In common practice, repair or replacement requires open-heart surgery with its attendant risks, expense, and extended recovery time. Open-heart surgery also requires cardiopulmonary bypass with risk of thrombosis, stroke, and infarction.

Mitral valve insufficiency results from various types of cardiac disease. Any one or more of the mitral valve structures, i.e., the anterior or posterior leaflets, the chordae, the papillary muscles or the annulus may be compromised by damage from disease or injury, causing the mitral valve insufficiency. Typically, in cases where there is mitral valve insufficiency, there is some degree of annular dilatation resulting in mitral valve regurgitation. Mitral valve regurgitation occurs as the result of the leaflets being moved away from each other by the dilated annulus. Thus, without correction, the mitral valve insufficiency may lead to disease progression and/or further enlargement and worsening of the insufficiency. In some instances, correction of the regurgitation may not require repair of the valve leaflets themselves, but simply a reduction in the size of the annulus. A variety of techniques have been used to reduce the diameter of the mitral annulus and eliminate or reduce valvular regurgitation in patients with incompetent valves.

Current surgical procedures to correct mitral regurgitation in humans include, a number of mitral valve replacement and repair techniques. Valve replacement can be performed through open-heart surgery, open chest surgery, or percutaneously. The native valve is removed and replaced with a prosthetic valve, or a prosthetic valve is placed over the native valve. The valve replacement may be a mechanical or biological valve prosthesis. The open chest and percutaneous procedures avoid opening, the heart and cardiopulmonary bypass. However, the valve replacement may result in a number of complications including a risk of endocarditis. Additionally, mechanical valve replacement requires subsequent anticoagulation treatment to prevent thromboembolisms.

As an alternative to valve replacement, various valve repair techniques have been used including quadrangular segmental resection of a diseased posterior leaflet, transposition of posterior leaflet chordae to the anterior leaflet, valvuloplasty with plication and direct suturing of the native valve, substitution, reattachment or shortening of chordae tendinae, and annuloplasty in which the effective size of the valve annulus is contracted by attaching a prosthetic annuloplasty ring to the endocardial surface of the heart around the valve annulus. The annuloplasty techniques may be used in conjunction with other repair techniques. Typically annuloplasty rings are sutured along the posterior mitral leaflet adjacent to the mitral annulus in the left atrium. The rings either partially or completely encircle the valve, and may be rigid, or flexible but nonelastic. All of these procedures require cardiopulmonary bypass, though some less, or minimally invasive techniques for valve repair and replacement are being developed.

Although mitral valve repair and replacement can successfully treat many patients with mitral valve insufficiency, techniques currently in use are attended by significant morbity and mortality. Most valve repair and replacement procedures require a thoracotomy, to gain access to the patient's thoracic cavity. Surgical intervention within the heart generally requires isolation of the heart and coronary blood vessels from the remainder of the arterial system and arrest of cardiac function. Open chest techniques with large sternum openings are typically used. Those patients undergoing such techniques often have scarring retraction, tears or fusion of valve leaflets, as well as disorders of the subvalvular apparatus.

Recently, other surgical procedures have been provided to reduce the mitral valve annulus using a less invasive surgical technique. According to this method, a prosthesis is transvenously advanced into the coronary sinus and deployed within the coronary sinus to reduce the diameter of the mitral valve annulus. The prosthesis then undergoes a change within the coronary sinus that causes it to assume a reduced radius of curvature, and as a result, to reduce the circumference of the mitral valve annulus. This may be accomplished in an open procedure or by percutaneously accessing the venous system by one of the internal jugular, subclavian or femoral veins.

While the coronary sinus implant provides a less invasive treatment alternative, the placement of the prosthesis within the coronary sinus may be problematic for a number of reasons. Sometimes the coronary sinus is not accessible. The coronary sinus on a particular individual may not wrap around the heart far enough to allow enough encircling of the mitral valve. Also, leaving a device in the coronary sinus may result in formation and breaking off of thrombus that may pass into the right atrium, right ventricle and ultimately the lungs causing a pulmonary embolism. Another disadvantage is that the coronary sinus is typically used for placement of a pacing lead, which may be precluded with the placement of the prosthesis in the coronary sinus.

It would be desirable, therefore, to provide a method and device for reducing cardiac valve regurgitation that use minimally invasive surgical techniques, and would overcome the limitations and disadvantages inherent in the devices described above.

SUMMARY OF THE INVENTION

One aspect of the present invention provides a system for treating mitral valve regurgitation comprising a delivery catheter with an expandable balloon located on the distal portion of the catheter and a mitral valve reshaping device disposed about the balloon. The reshaping device comprises a body having a plurality of anchoring barbs extending from the body.

Another aspect of the invention provides a reshaping device wherein the anchoring barbs on the anterior side of the body of the reshaping device are shorter than the anchoring barbs on the posterior side.

Another aspect of the invention provides a reshaping device wherein the device has no anchoring barbs on the anterior side of the body of the reshaping device.

Another aspect of the invention provides a method for treating mitral valve regurgitation. The method comprises using a catheter to deliver, adjacent to a mitral valve, a reshaping device having body and a plurality of attachment barbs extending from the body. The method further comprises retracting a sheath portion of the catheter, and optionally, moving the barbs from a restrained position to an insertion position in response to the retracting of the sheath. The method further comprises expanding a balloon portion of the catheter while the attachment barbs are in the insertion and causing the barbs to insert into the annulus of the mitral valve in response to the expansion of the balloon. The method further comprises contracting the balloon and causing the body of the reshaping device to move from a deployment configuration to a resting configuration in response to the contraction of the balloon. Finally, the method comprises reshaping the mitral valve based on the movement of the body of the reshaping device to the resting configuration.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

DETAILED DESCRIPTION

The invention will now be described by reference to the figures wherein like numbers refer to like structures. The terms "distal" and "proximal" are used herein with reference to the treating clinician during the use of the catheter system; "Distal" indicates an apparatus portion distant from, or a direction away from the clinician and "proximal" indicates an apparatus portion near to, or a direction towards the clinician. Additionally, the term "annuloplasty" is used herein to mean modification/reconstruction of a defective heart valve.

The current invention discloses devices and methods for treating regurgitation in cardiac valves. While these devices and methods are described below in terms of being used to treat mitral regurgitation, it will be apparent to those skilled in the art that the devices could be used on other cardiac valves also.

Figure 1:
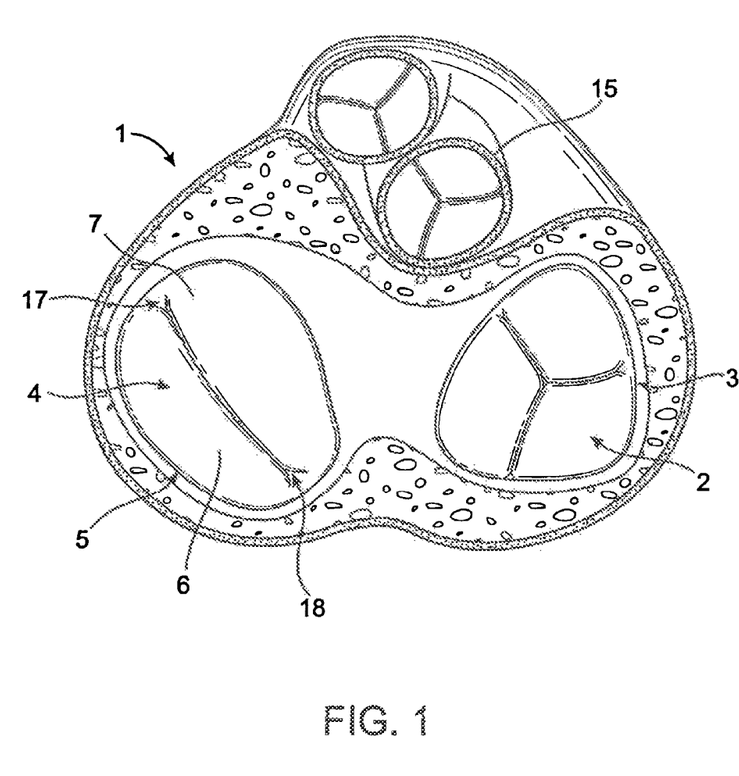
FIG. 1 is a cross-sectional schematic view of a heart showing the location of the heart valves.

Referring to the drawings, FIG. 1 shows a schematic cross-sectional view of a heart 1 having tricuspid valve 2 and tricuspid valve annulus 3. Mitral valve 4 is adjacent mitral valve annulus 5. Mitral valve 4 is a bicuspid valve having anterior cusp 7 and posterior cusp 6. Anterior cusp 7 and posterior cusp 6 are often referred to, respectively, as the anterior and posterior leaflets. FIG. 1 also shows the aorta 15, which is located adjacent the wall of the left atrium on the anterior side of the mitral valve. Also shown in the figure are the posterior commissure 17 and the anterior commissure 18.

Figure 2:
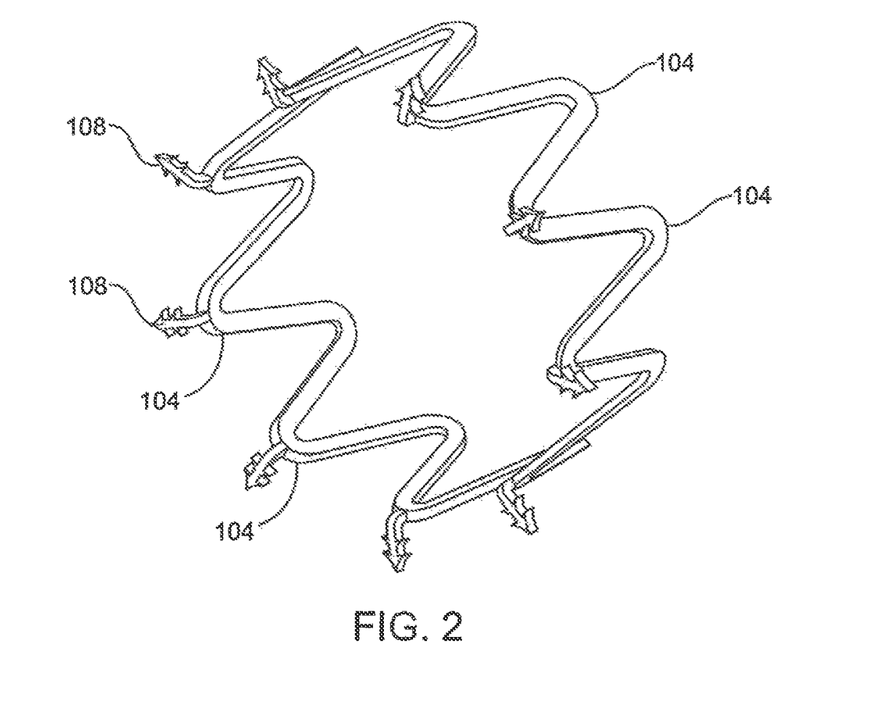
FIGS. 2 through 4 are illustrations of cardiac valve reshaping devices in accordance with the present invention.
Figure 3:
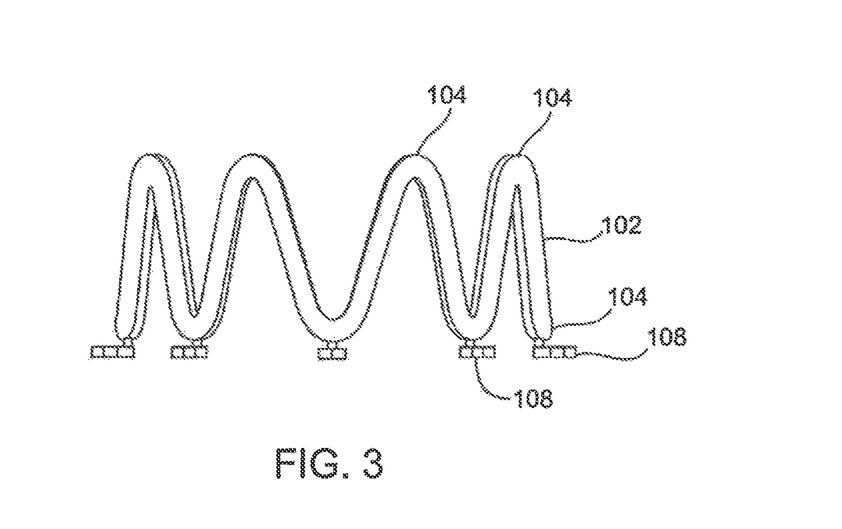

FIGS. 2 and 3 are illustrations showing a reshaping device for treating mitral valve. Reshaping device includes a plurality of struts 102 in a generally cylindrical configuration that comprise the main body of the reshaping device. Struts 102 are joined together by apexes 104, and form a generally serpentine pattern.

A plurality of barbs 108 are disposed at the apexes 104 on a distal end of reshaping device. In one embodiment of the invention, the barbs 108 are moveable and can be directed axially, parallel to the central axis of reshaping device, or can be directed radially outward. Barbs 108 are portrayed in radially directed configuration in FIGS. 2 and 3. The purpose of barbs 108 is to anchor reshaping device to the annulus of the mitral valve. In one embodiment of the invention, a mechanical device such as an expandable balloon is used to expand device to the fully expanded configuration shown in FIG. 3.

In some hearts, the tissue of the annulus and surrounding wall of the heart is very thin. This can present a problem on the anterior side of the heart because the aorta is located on the anterior side of the mitral valve. One embodiment of the device eliminates the potential for puncturing the aorta by not having barbs on the portion of the device that will be on the anterior side of the mitral valve.

In another embodiment of the device, the barbs on the portion of the device that will be on the anterior side of the mitral valve are shorter than the barbs on the portion of the device that will be on the posterior side of the mitral valve. In one embodiment of the invention, barbs 108 comprise NITINOL, and move independently of the movement or configuration of the body of device.

The devices of the current invention can include radiopaque material or other markers that will allow a clinician to properly align the anterior and posterior sides of the device with the anterior and posterior portions of the mitral valve respectively. The devices of the current invention can also include markers or other material to indicate the distal and proximal ends of the device.

Figure 4:
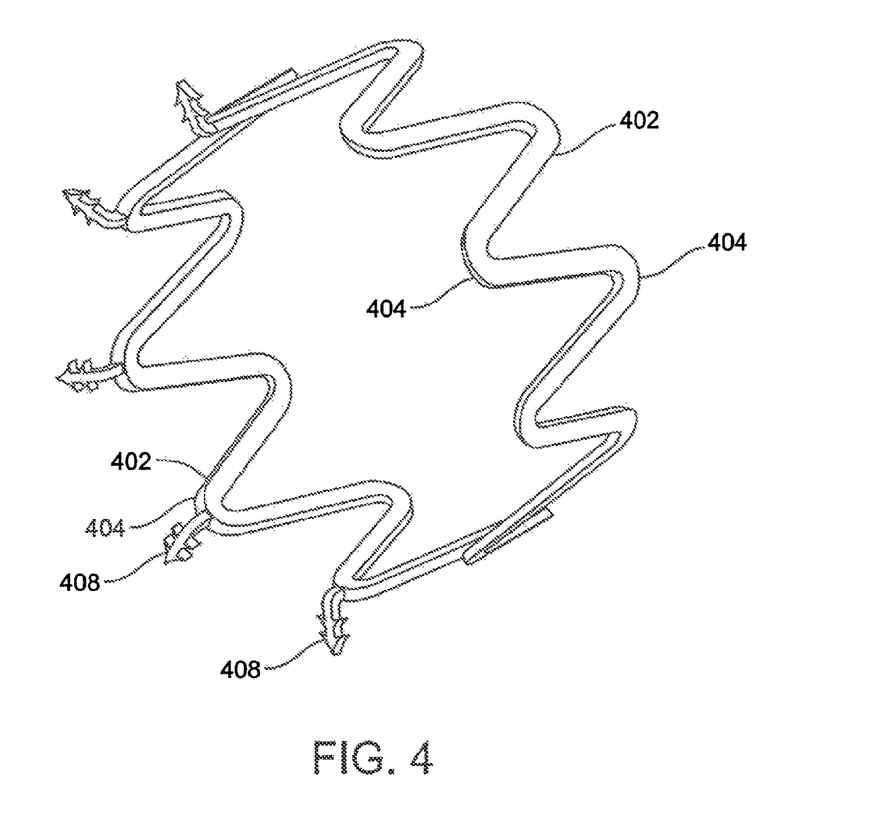

FIG. 4 is a schematic representation of another embodiment of a reshaping device in a resting configuration. In this configuration, radius of the device is greater than in a compressed configuration but smaller than when the device is in the fully expanded deployment configuration. The device illustrated in FIG. 4 is a generally serpentine ring having a plurality of struts 402 in a generally cylindrical configuration that comprise the main body of the reshaping device. Struts 402 are joined together by apexes 404, and form the generally serpentine pattern. The reshaping device includes a plurality of barbs 408 on the side of the device that would be implanted on a posterior portion of a mitral valve annulus and no barbs on the portion of the device that will be implanted on the anterior portion of the mitral valve annulus. The barbs 408 extend radially from the central axis of device in this resting configuration.

The devices of the current invention can be made from any biocompatible material having suitable shape memory properties. In one embodiment the device is self-expandable and it is set in the resting configuration. The device can then be crimped onto a delivery catheter and delivered to a location adjacent a cardiac valve annulus. The device will expand to a delivery configuration when a restraining sheath is removed. A balloon can then be used to over-expand the device and drive the barbs into the valve annulus. After the balloon is deflated the device then resumes the resting configuration, thereby causing the shape of the valve annulus to be altered.

In another embodiment of the invention, the device is balloon expandable and it is set in the resting configuration similar to the device described immediately above. The device is crimped onto a delivery catheter, delivered to a cardiac valve, expanded to, a deployment configuration, and contracted to a resting configuration in a manner similar to the device described immediately above.

In one embodiment of the invention, reshaping device comprises a biocompatible shape-memory material, such as NITINOL. Reshaping device can be fabricated by laser or mechanical cutting methods well known, in the art. Next, device is formed into the resting configuration such that the diameter of device in this configuration is the desired diameter of the mitral valve annulus following treatment. Also, barbs are placed in the radially extended position. The NITINOL comprising device is then set in the resting configuration using heat or any other appropriate means. The device can be compressed from the resting configuration and the barbs can be moved between a longitudinally extended delivery position and a radially extended insertion position independently of the diameter of the body of the device by exerting or releasing a restraining force on the barbs. However, when all forces are removed, device will spontaneously assume the resting configuration.

Figure 5:
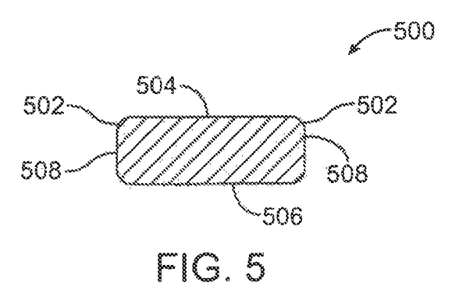
FIGS. 5 through 7 are cross-sectional views of exemplary protective struts for use in the mitral valve reshaping device illustrated in FIGS. 1 to 3, in accordance with the invention.
Figure 6:
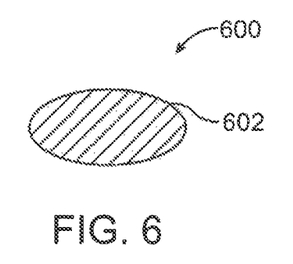
Figure 7:
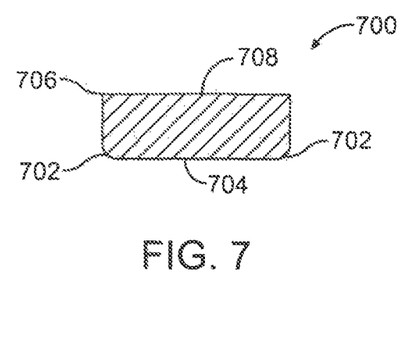

In some embodiments of the current invention, the longitudinal struts 102 have dulled or rounded edges so that the strut will not damage the delicate cardiac tissue of the valve or surrounding area of the heart. FIGS. 5 through 7 illustrate various embodiments of such struts having rounded or dulled edges. FIG. 5 illustrates a protective strut 500 having a transverse cross section with rounded edges 502 on the outer surface 504 and on the inner surface 506. Rounded edges 502 exist as arched transitions between flat planes 504 and 508.

FIG. 6 illustrates a protective strut 600. In this embodiment, protective strut 600 has an oval shaped transverse cross section with symmetrical rounded ends 602. In one embodiment of the invention having struts with an oval shaped transverse cross section, the interior and exterior surfaces are essentially flat, and in another they are gently rounded. In another embodiment, the transverse cross section of the struts is circular or round in shape. FIG. 7 illustrates a protective strut 700. In this embodiment, protective strut 700 has an elongate cross section with rounded edges 702 on the outer surface 704 that contacts the valve annulus and surrounding cardiac tissue, and squared edges 706 on the inner surface 708.

Various methods for creating rounded edges on struts are known in the art. One such method is electropolishing, where an electric current is run through the metallic strut in a conductive aqueous bath made of salts that are similar to the base metal being polished. A cathode is positioned in the bath. As the electricity jumps from the strut (acting as an anode) to the cathode, material is removed. Material preferentially comes off of the peaks, which are also the square edges of the strut. As the material is removed from the square edge, it becomes rounded or dull.

Another method for rounding off the square edges of struts is tumbling the strut material in a mixture of media that typically includes silicon carbide and water with silicon carbide impregnated alumina or plastic. The action of the media rubbing against the device removes the square cut edges from the strut.

Figure 8:
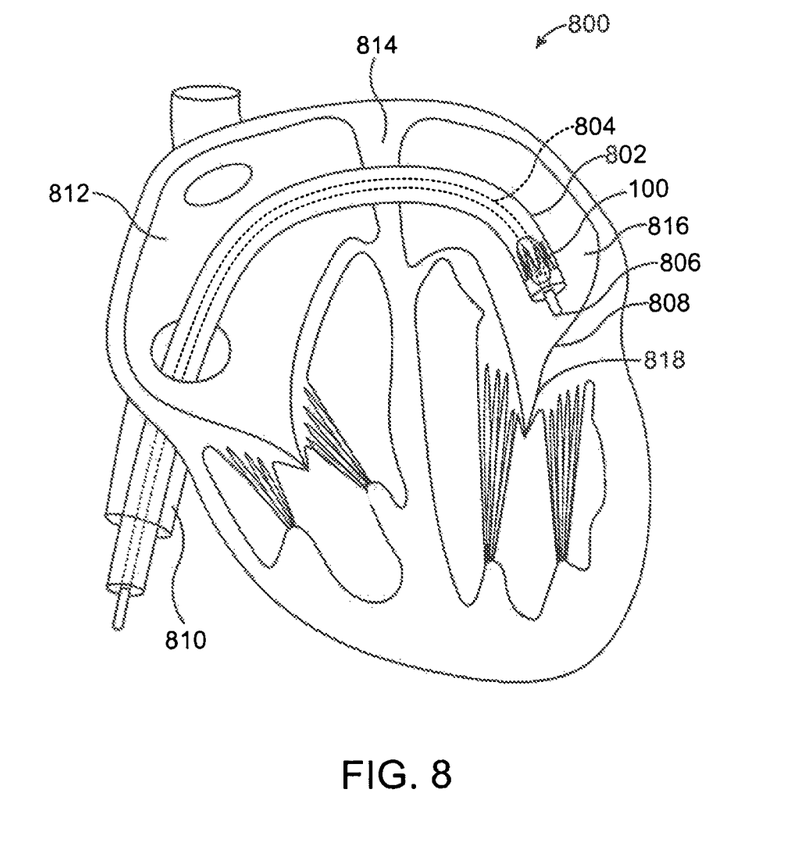
FIGS. 8 and 9 are illustrations showing the placement of a reshaping device adjacent to a mitral valve, in accordance with the invention.

FIG. 8 is a schematic view of the distal portion of system 700 for treating mitral valve regurgitation using minimally invasive surgical techniques, in accordance with the present invention. Mitral valve reshaping device is contained within a sheath 702 attached to the distal portion of delivery catheter 704. Delivery catheter 704 is flexible, and configured so that it can be inserted into the cardiovascular system of a patient. Appropriate catheters are well known in the art, and are made of flexible biocompatible materials such as polyurethane, polyethylene, nylon and polytetrafluoroethylene (PTFE). In order to facilitate passage through the vascular system, distal sheath 702 may have greater lateral flexibility than the tubular body of catheter 704. In one embodiment of the invention, an inflatable balloon is attached to the distal portion of catheter 704, and connected by a lumen (not shown) to a reservoir of inflation fluid at the proximal end of catheter 704.

Mitral valve reshaping device is disposed about the exterior surface of an expandable balloon on the distal portion of delivery catheter 704 and compressed to its deployment configuration. Anchoring barbs are extended axially, parallel to the central axis of reshaping device. Reshaping device is then placed within sheath 702 of catheter 704 near catheter distal tip 706.

In one embodiment of the invention, sheath 702 is retractable, as is well known in the art. While sheath 702 covers barbs, it maintains the barbs in an axially extended configuration. When sheath 702 is retracted, barbs spontaneously assume a radially extended deployment configuration.

To deliver device adjacent to the mitral valve, distal tip 706 of delivery catheter 704 containing device is inserted into the vascular system of the patient. To reach the mitral valve, catheter tip 706 may be inserted through the femoral vein into the common iliac vein, through inferior vena cava 710, and into right atrium 712. Alternatively, catheter 704 may be inserted into the subclavian vein, through superior vena cava, and into right atrium 712. Next, transeptal wall 714 between right atrium 712 and left atrium 716 is punctured with a guide wire or other puncturing device and distal tip 706 of delivery catheter 704 is advanced through the septal perforation and into left atrium 716 and placed in proximity to annulus 708 of mitral valve 718.

Another possible delivery path would be through the femoral artery into the aorta, through the aortic valve into the left ventricle, and then through the mitral valve into the left atrium. Yet another possible path would be through the left or right pulmonary vein directly into the left atrium. The placement procedure, using any of these vascular routes, is preferably performed using fluoroscopic or echocardiographic guidance.

Before the balloon is inflated, the collapsed device is placed in the left atrium such that the distal portion of the device is on the same plane as the mitral valve annulus. The sheath 702 is retracted, the barbs assume a radially extended deployment configuration, and a balloon is inflated to expand the device to a deployment configuration and drive the barbs into the mitral valve annulus. Once the balloon is deflated, the device will contract into a resting configuration and alter the shape of the mitral valve annulus.

Figure 9:
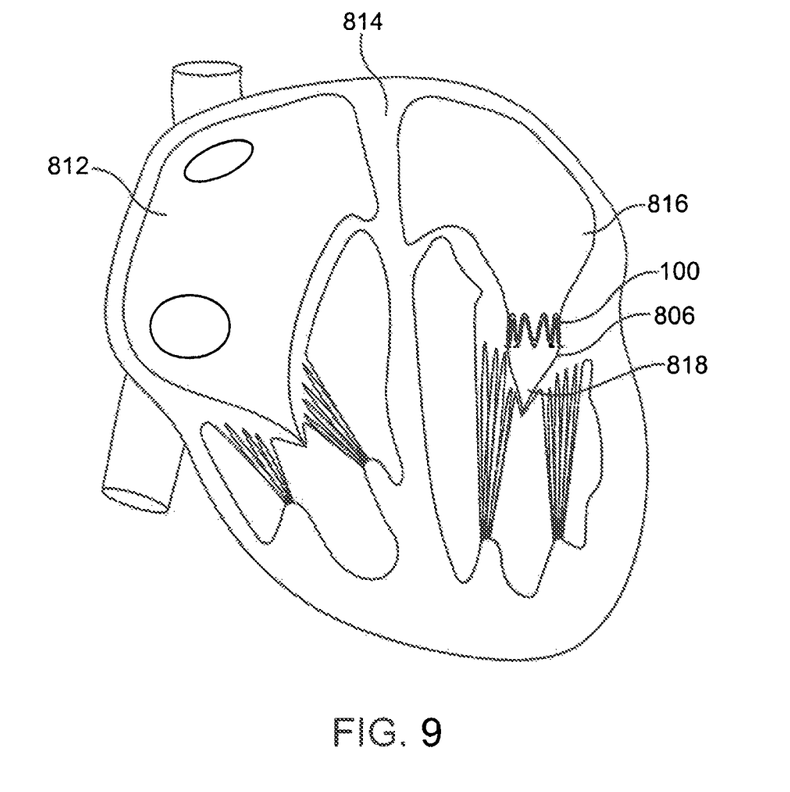

FIG. 9 shows the device of FIG. 8 after it has been implanted in a mitral valve according to the current invention as described immediately above. The barbs extend radially from the device and into the mitral valve annulus. The device has contracted into a resting configuration such that the shape of the mitral valve annulus has been altered and any mitral regurgitation has been reduced.

Figure 10:
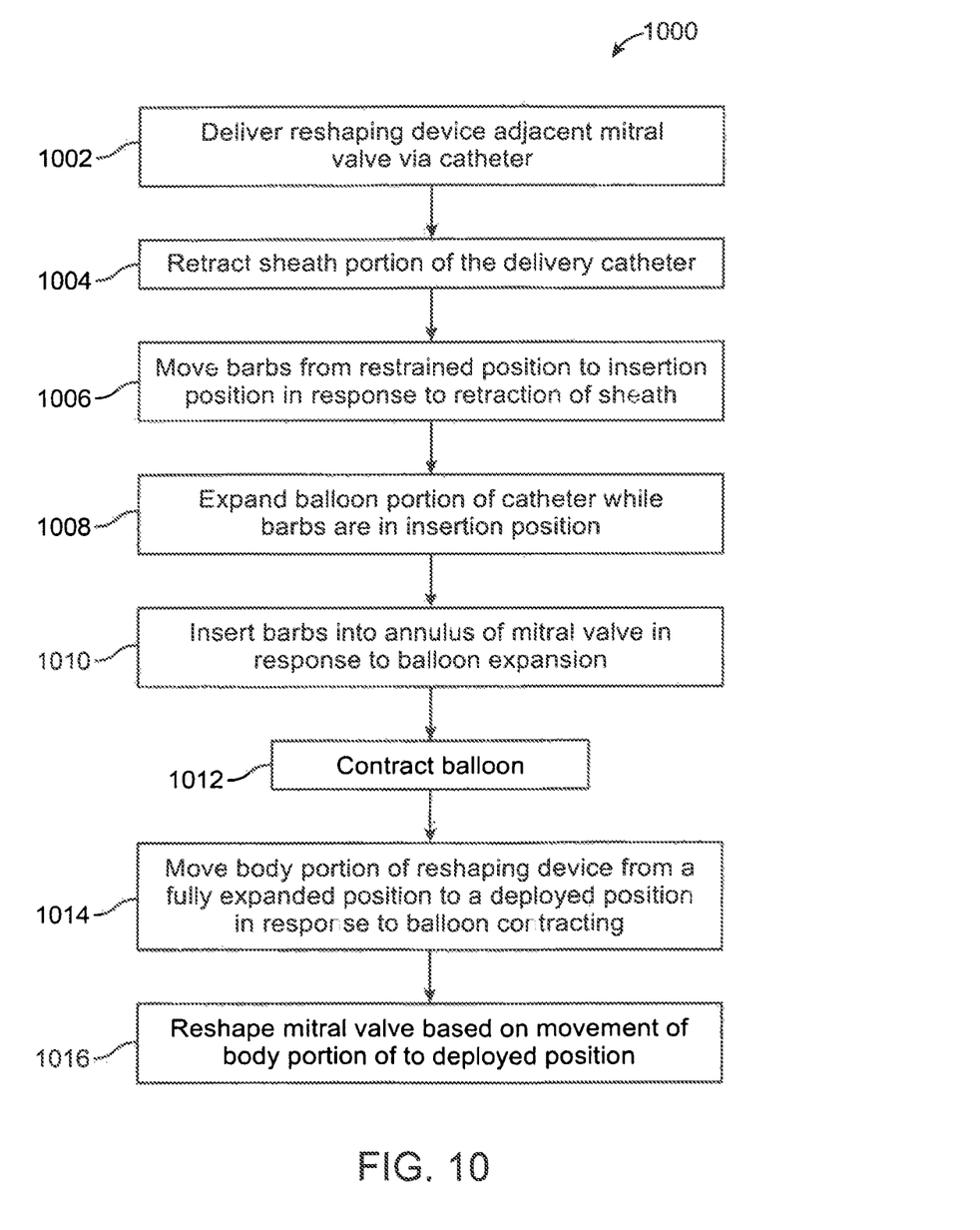
FIG. 10 is a flow diagram of a method of treating mitral valve regurgitation in accordance with one aspect of the invention.

FIG. 10 is a flowchart illustrating method 1000 for treating mitral valve regurgitation, in accordance with one aspect of the invention. As discussed above, a delivery catheter is inserted into the vascular system of the patient, passed through the right atrium, and into left atrium, adjacent to mitral valve annulus (Block 1002).

Next, a cardiac valve reshaping device is deployed from a catheter (Block 1004). A sheath is retracted and the barbs spontaneously assume an insertion configuration, that is radially extended from the longitudinal axis of the reshaping device as indicated in (Block 1006). Next, the reshaping device is oriented so that an anterior side of the device will be adjacent to the anterior side of mitral valve annulus.

Next, the expandable balloon on the delivery catheter is expanded (Block 1008), causing the body of the device to be mechanically expanded to its deployment configuration. The barbs are inserted into the tissue of the annulus of the mitral valve annulus.

Once the reshaping device is secured to the valve annulus by the anchoring barbs, the balloon is contracted (Block 1012). As soon as the force applied to the body of the device by the expanded balloon is removed, the device assumes its resting configuration (Block 1014).

Because the reshaping device, is securely fastened to the annulus of the mitral valve, the diameter of annulus is reduced correspondingly, as indicated in (Block 1016). The diameter of mitral valve annulus is reshaped sufficiently so that the anterior and posterior leaflets close during ventricular contraction, and regurgitation of blood is reduced. Improvement in the valve closure can be evaluated by checking for decreased pressure in the left atrium. Finally, the delivery catheter is withdrawn from the body of the patient.

While the invention has been described with reference to particular embodiments, it will be understood by one skilled in the art that variations and modifications may be made in form and detail without departing from the spirit and scope of the invention.

What is claimed is:

1. A method for reshaping a mitral valve annulus comprising:
    advancing the distal tip of a delivery catheter comprising a delivery sheath containing a prosthesis through a pulmonary vein, through a left atrium to the mitral valve annulus, the prosthesis including a ring and a plurality of anchor members extending from one end of the ring, the delivery sheath containing the ring in a compressed configuration during the advancing step;
    retracting the delivery sheath from the prosthesis, wherein when the delivery sheath is retracted, the ring self-expands from the compressed configuration to a pre-deployment configuration;
    expanding an inner diameter of the ring to a deployment configuration to drive the anchor members into the mitral valve annulus to secure the prosthesis to the mitral valve annulus; and
    reducing the inner diameter of the ring to a resting configuration to reshape the mitral valve annulus, wherein the ring is formed of a shape memory material, wherein the step of reducing the inner diameter of the ring to the resting configuration is achieved by the ring self-contracting to the resting configuration due to the shape-memory material,
    wherein the ring in the pre-deployment configuration has a smaller diameter than the ring in the deployment configuration and a larger diameter than the ring in the compressed configuration.

2. The method of claim 1, further comprising using fluoroscopic guidance or echocardiographic guidance for the step of advancing the distal tip of the catheter to the mitral valve annulus.

3. The method of claim 1, wherein when the delivery sheath is retracted the anchor members assume a radially extended insertion configuration.

4. The method of claim 1, wherein the step of expanding the inner diameter of the ring to the deployment configuration to drive the anchor members into the mitral valve annulus comprises inflating a balloon to expand the ring.

5. The method of claim 1, wherein the ring is a serpentine ring.

6. The method of claim 1, wherein the anchor members comprise barbs.

7. The method of claim 1, wherein the anchor members are disposed on only a posterior portion of the ring, and wherein the step of expanding the inner diameter of the ring to the deployment configuration comprises expanding the inner diameter of the ring to the deployment configuration to drive the anchor members into only a posterior portion of the mitral valve annulus.

8. A method for reshaping a mitral valve annulus comprising:
    advancing the distal tip of a delivery catheter comprising a delivery sheath containing a prosthesis in a compressed configuration through a pulmonary vein, through a left atrium to the mitral valve annulus, wherein the prosthesis is a closed ring;
    retracting the delivery sheath from the prosthesis, wherein the prosthesis comprises a plurality of anchor members extending from one end of the prosthesis, wherein when the delivery sheath is retracted the anchor members assume a radially extended insertion configuration;
    expanding an inner diameter of the prosthesis to a deployment configuration to drive the anchor members in the radially extended insertion configuration into the mitral valve annulus to secure the prosthesis to the mitral valve annulus; and
    reducing the inner diameter of the prosthesis to a resting configuration to reshape the mitral valve annulus.

9. The method of claim 8, further comprising using fluoroscopic guidance or echocardiographic guidance for the step of advancing the distal tip of the catheter to the mitral valve annulus.

10. The method of claim 8, wherein when the delivery sheath is retracted, the prosthesis self-expands from the compressed configuration to a pre-deployment configuration having a smaller diameter than the prosthesis in the deployment configuration.

11. The method of claim 8, wherein the prosthesis is balloon expandable.

12. The method of claim 8, wherein the step of expanding the inner diameter of the prosthesis to the deployment configuration to drive the anchor members into the mitral valve annulus comprises inflating a balloon to expand the prosthesis.

13. The method of claim 8, wherein the prosthesis is a serpentine ring.

14. The method of claim 8, wherein the anchor members comprise barbs.

15. The method of claim 8, wherein the anchor members are disposed on only a posterior portion of the prosthesis, and wherein the step of expanding the inner diameter of the prosthesis to the deployment configuration comprises expanding the inner diameter of the prosthesis to the deployment configuration to drive the anchor members into only a posterior portion of the mitral valve annulus.

\* \* \* \* \*